United States Patent [19]
Gemma, Jr. et al.

[11] Patent Number: 5,615,766
[45] Date of Patent: Apr. 1, 1997

[54] SUTURE PACKAGE RETENTION SLEEVE AND PROCEDURE KIT

[75] Inventors: Edward A. Gemma, Jr., Milford, Conn.; Andrew P. Stellon, Rivervale, N.J.

[73] Assignee: United States Surgical Corporation, Norwalk, Conn.

[21] Appl. No.: 435,743

[22] Filed: May 5, 1995

[51] Int. Cl.$^6$ .............................. A61B 17/06; B65D 85/48
[52] U.S. Cl. ...................... 206/63.3; 206/453; 206/484.1
[58] Field of Search .................................. 206/63.3, 63.5, 206/425, 439, 453, 484.1

[56] References Cited

U.S. PATENT DOCUMENTS

| | | |
|---|---|---|
| 4,063,638 | 12/1977 | Marwood ................................. 206/63.3 |
| 4,249,656 | 2/1981 | Cerwin et al. ........................ 206/63.3 |
| 4,253,563 | 3/1981 | Komarnycky ......................... 206/63.3 |
| 5,335,775 | 8/1994 | Scanlon et al. . |
| 5,509,533 | 4/1996 | Veenstra ................................. 206/425 |

FOREIGN PATENT DOCUMENTS 0607051  7/1994  European Pat. Off. .

Primary Examiner—David T. Fidei

[57] ABSTRACT

An adjustable suture package retention sleeve and procedure kit is provided which supports a plurality of suture packages for sterilization and subsequent transport, storage and use. Suture package sheaths are contained within the suture package retention sleeve which is adjustable depending on the number of suture package sheaths. The adjustable suture package retention sleeve includes a first and second panel foldably interconnected along the lower edge to form a pocket for receipt of the suture package sheaths. The sleeves further contains first and second interlocking flaps formed on opposite end portions of the first panel to secure the second panel adjacent the first panel and define a pocket therebetween. The procedure kit contains a plurality of suture package sheaths each containing various types and styles of suture packages disposed therein. The adjustable suture package retention sleeve containing the suture package sheaths and suture packages, may be inserted within a pouch for sterilization and subsequently inserted in a box for transport, storage and use.

6 Claims, 5 Drawing Sheets

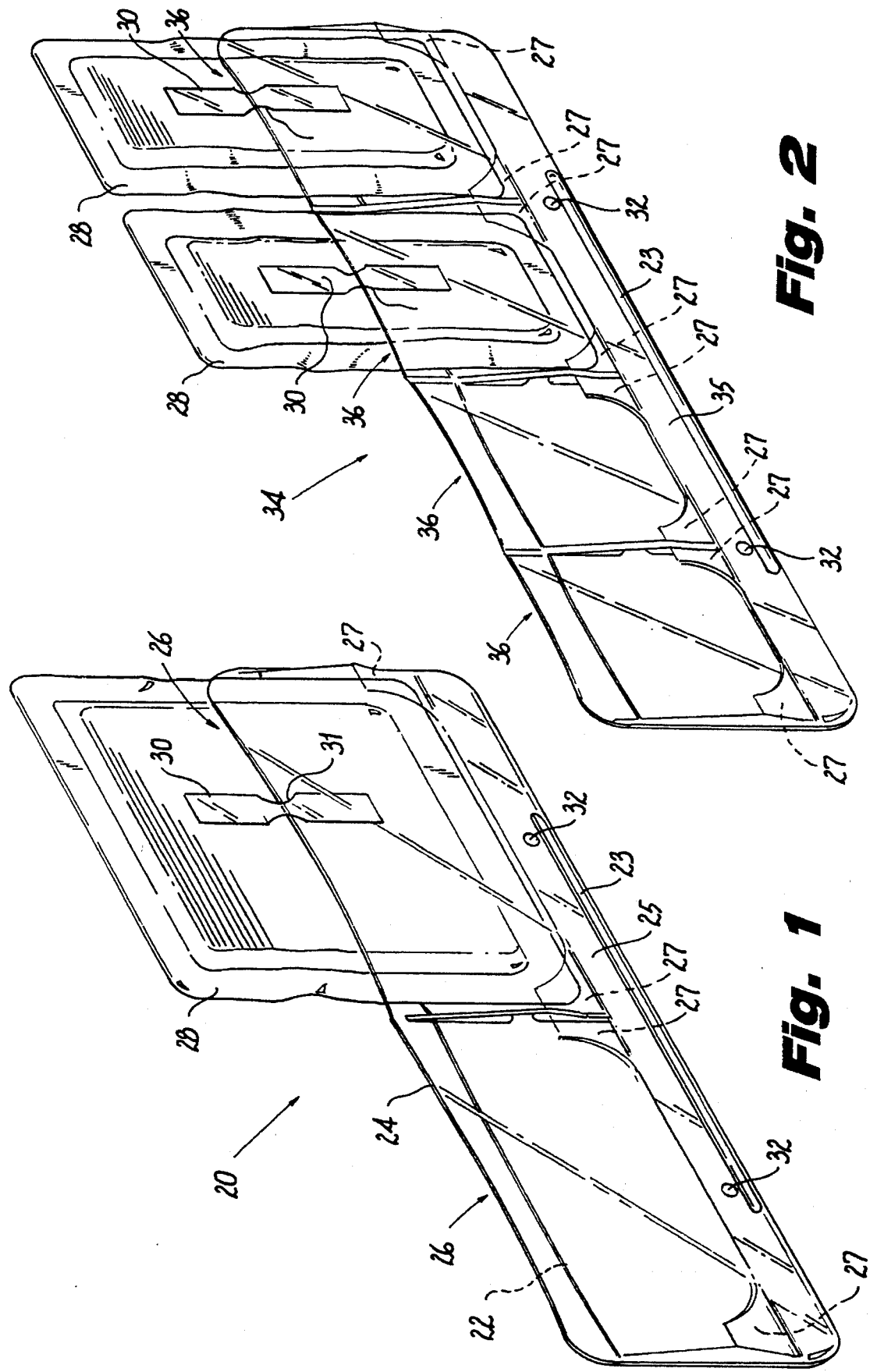

SUTURE PACKAGE RETENTION SLEEVE AND PROCEDURE KIT

BACKGROUND

1. Technical Field

The technical field relates to storage and packaging of surgical devices and more particularly, to an adjustable suture package retention sleeve and procedure kit for organized sterilization, storage and presentation of sutures and the like.

2. Background of Related Art

Modern surgical procedures draw upon a wide variety of types and sizes of sutures. These sutures are usually contained in individual retainers or foil laminate envelopes wherein the suture is wound in a figure 8 pattern on a paper retainer as shown for example in U.S. Pat. Nos. 4,249,656, 4,253,563 and 4,063,638. Other patterns such as coils, racetracks, etc., may also be used. The size and type of the suture is typically printed on the enclosure envelopes for ease of identification.

Depending upon the type of surgical procedure to be performed, a wide selection of sutures of different types and sizes must be available and readily accessible to the surgical staff. Currently, a large supply of different types and sizes of individually packaged sterilized sutures are maintained in the operating area. The packages are typically arranged in loose stacks according to type and size in an area adjacent the surgical instruments. However, picking and recording the sutures used during the surgical procedure may be very time consuming. Further, these loose stacks have a tendency to become mixed and disorganized during surgery, particularly extended surgery, making it difficult and time consuming to locate the proper suture package with the type and size of suture required by the surgeon.

One device designed to present a plurality of stacked suture packages is disclosed in U.S. Pat. No. 5,335,775 to Scanlon et at., the disclosure of which is incorporated by reference herein. Scanlon et al. relates to a suture display rack and procedure kit for organizing suture packages. The rack is a generally u-shaped member within which the suture packages can be loosely held. Additionally, the suture packages can be contained in separate sheaths, or hinged to a wall of the rack, for ease of review and removal.

While the rack disclosed in Scanlon et al. is useful, it would be highly desirable to have a suture package retention sleeve and procedure kit which contains a plurality of interlocked suture package sheaths, each containing preselected suture packages, for ease of sterilization, transport, display and organization during use. It would also be desirable to have a suture package retention sleeve and procedure kit which utilizes less raw materials than conventional kits.

These and other highly desirable and unusual results are accomplished by providing an adjustable suture package retention sleeve and procedure kit for storing and sterilizing a plurality of suture packages contained within the suture package sheaths.

SUMMARY

An adjustable sleeve for retaining suture package sheaths is provided and includes a first panel having first and second flaps foldably formed on opposite end portions thereof and having a lower edge, and a second panel foldably interconnected to the first panel along the lower edge. The first and second flaps are configured for interlocking engagement such that when the second panel is folded adjacent the first panel and the first and second flaps are interlocked, the first and second interlocked flaps hold the second panel adjacent to the first panel to define a pocket therebetween for receipt of a suture package sheath therein.

Preferably, the first flap has an aperture therein and the second flap has a strap extending therefrom. The strap is configured for insertion through the aperture to thereby engage the first flap with the second flap.

The strap preferably includes a first segment and a second segment foldably connected to the first segment and releasably engagable therewith, such that when the strap is inserted through the aperture and the second segment is folded adjacent the first segment and engaged therewith, the first and second flaps are maintained in interlocking engagement.

In order to secure the first segment to the second segment, the first segment may include an aperture formed therein and the second segment may have a tab formed thereon, and engagable with the aperture of the first segment to releasably engage the second segment with the first segment.

A suture package procedure kit is provided and includes at least one suture package sheath having a retaining pocket formed therein, a suture package disposed in the retaining pocket and an adjustable sleeve including first and second panels foldably interconnected for receipt of the suture package sleeve therebetween. The first panel includes first and second interlocking flaps formed at opposite ends of the first panel. A sterilizable pouch is also provided for receipt of the suture package sheath and adjustable sleeve.

The suture package procedure kit may further include a retention member releasably engagable with the suture package and the suture package sheath to releasably secure the suture package within the suture package sheath.

At least one flexible I-member insertable through openings formed within each of the suture package sheaths may be provided to maintain the sheaths in connected relationship.

There is also provided a method of displaying a plurality of suture packages in sterile condition by providing a sheath having at least one retaining portion formed therein, loading at least one suture package into the retaining portion and securing the sheath at least partially within a sterilizable sleeve having interlocking end portions. The method further includes placing the sleeve within a sterilizable pouch and sterilizing the sleeve, sheath and suture package.

BRIEF DESCRIPTION OF THE DRAWINGS

Various embodiments are described herein with reference to the drawings, wherein:

FIG. 1 is a perspective view of an alternate embodiment of a suture package sheath illustrating a single suture package disposed therein and a retention member to secure the suture package;

FIG. 2 is a perspective view of a further alternate embodiment of a suture package sheath with two suture packages secured therein;

3

Figure 4:
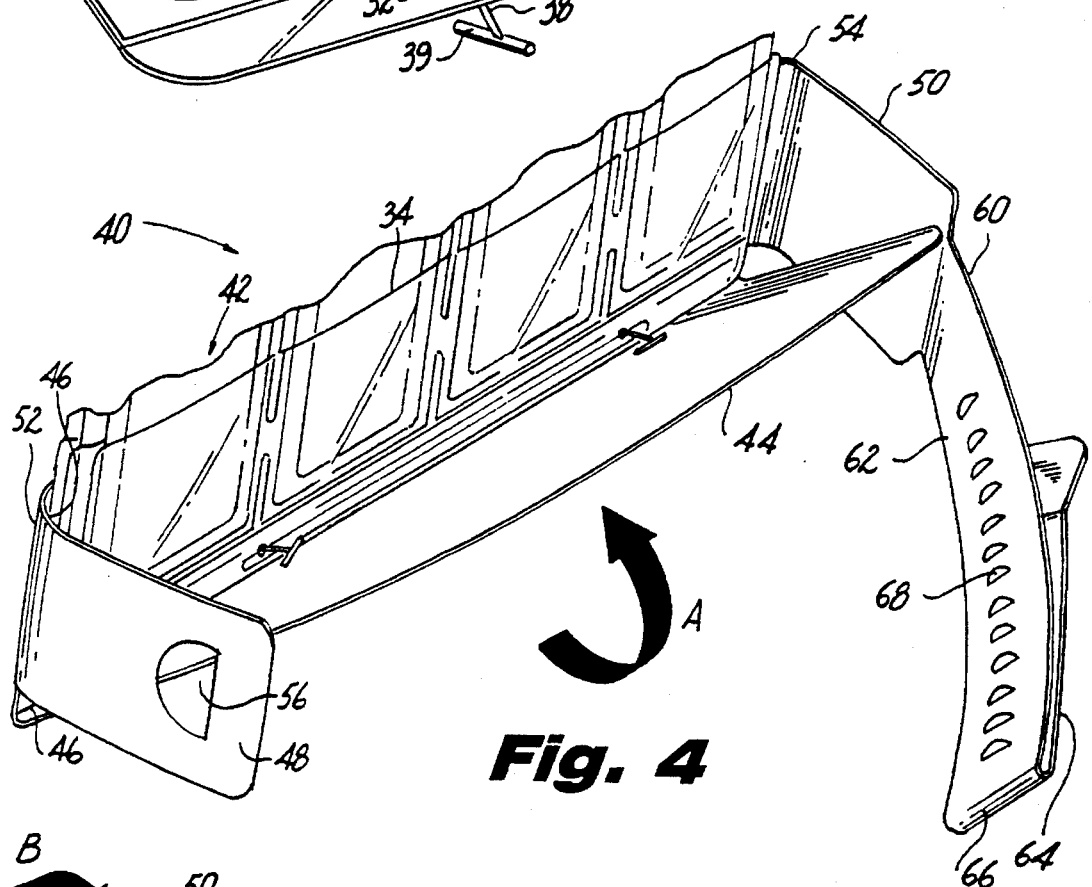
FIG. 4 is a perspective view of an adjustable suture package retention sleeve in a partially folded condition.
Figure 6:
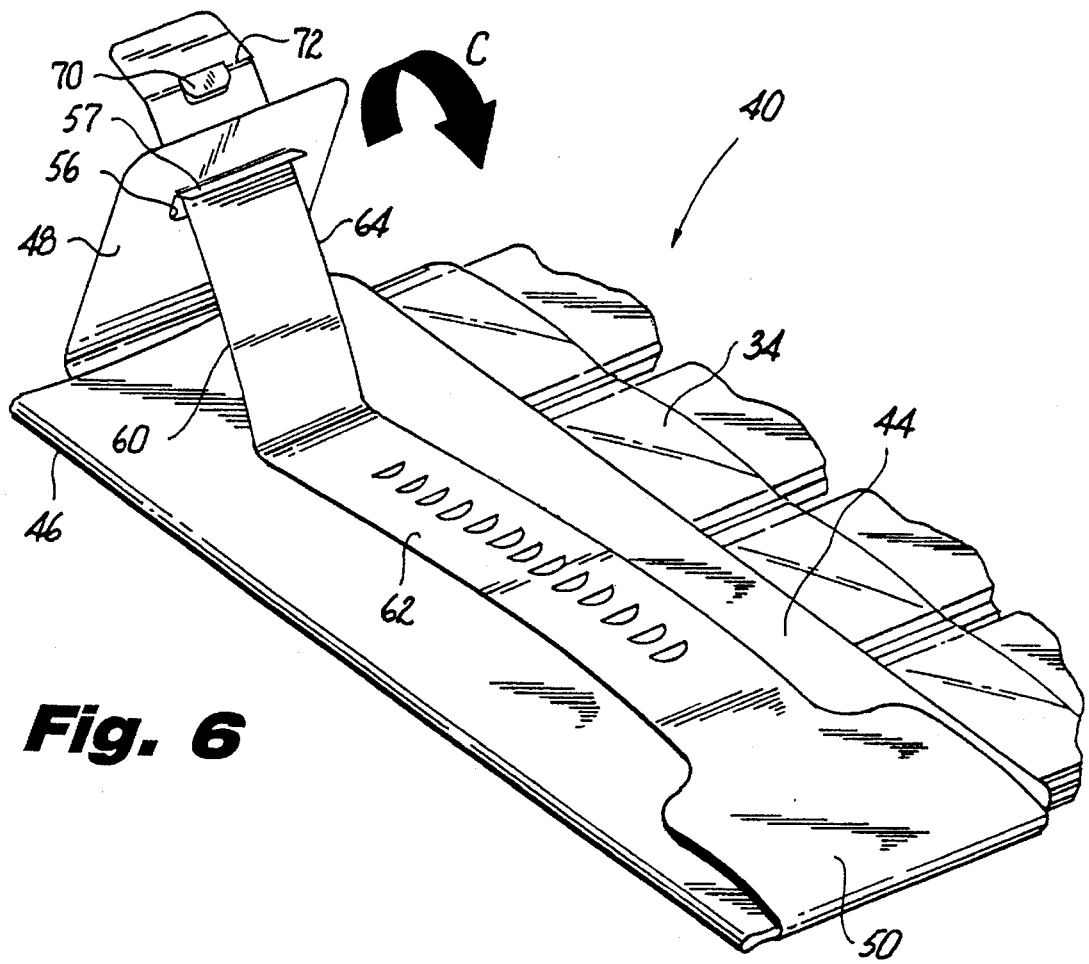
Figure 7:
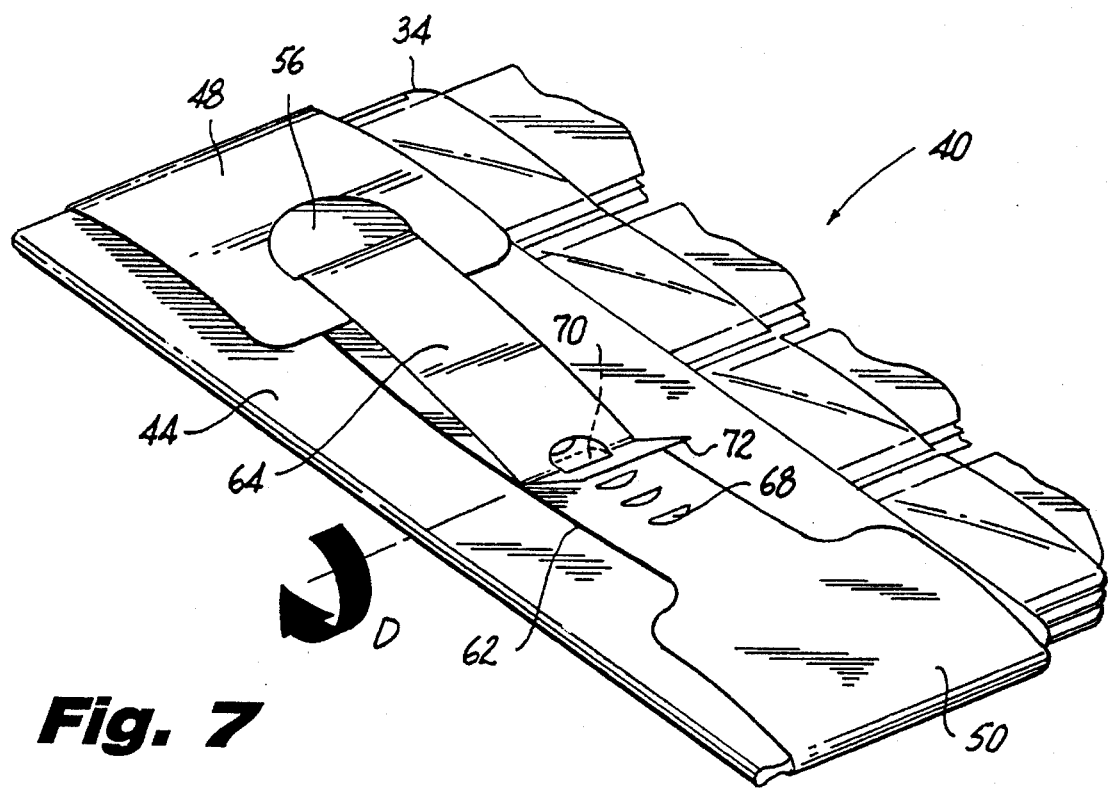
Figure 8:
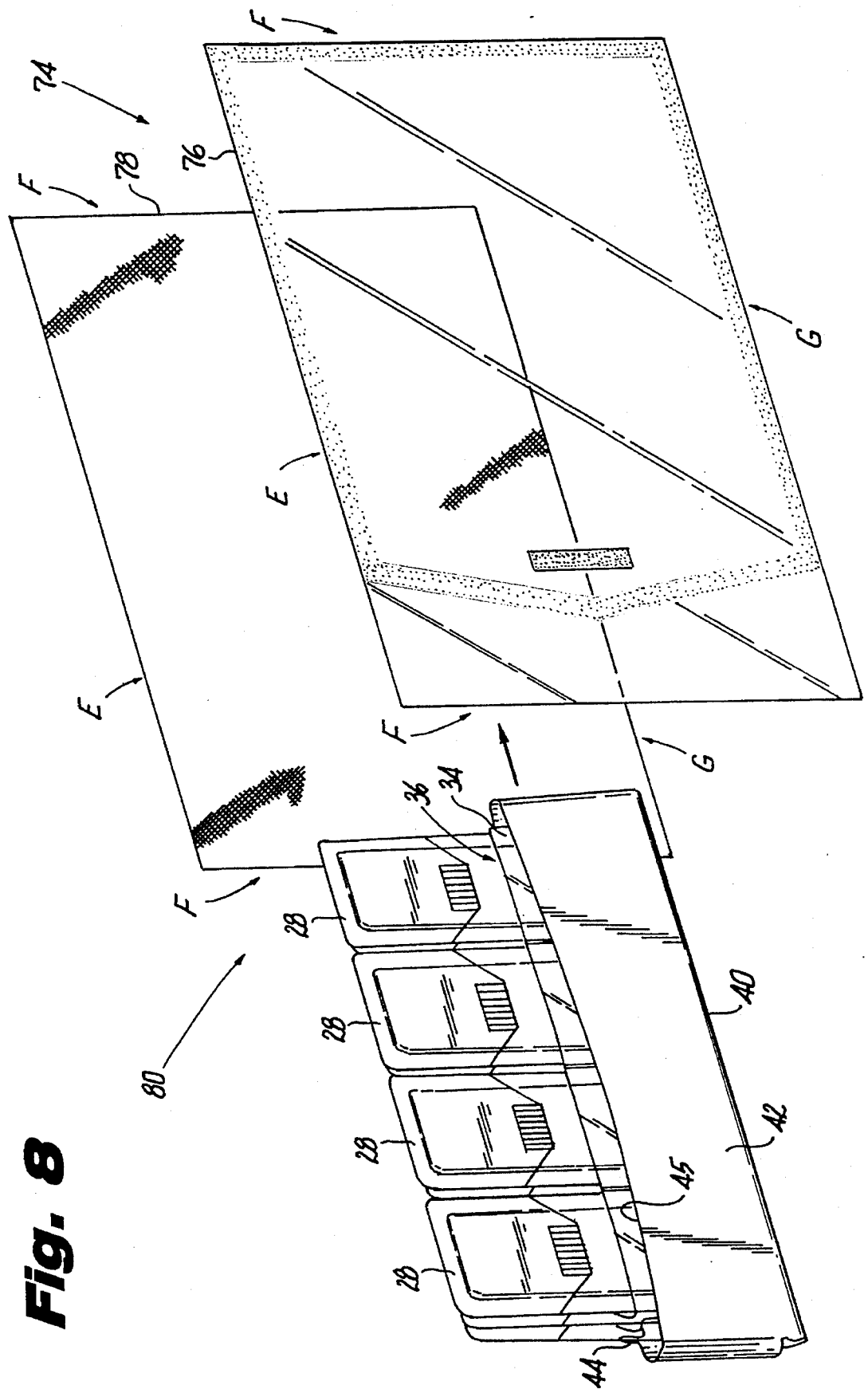
Figure 9:
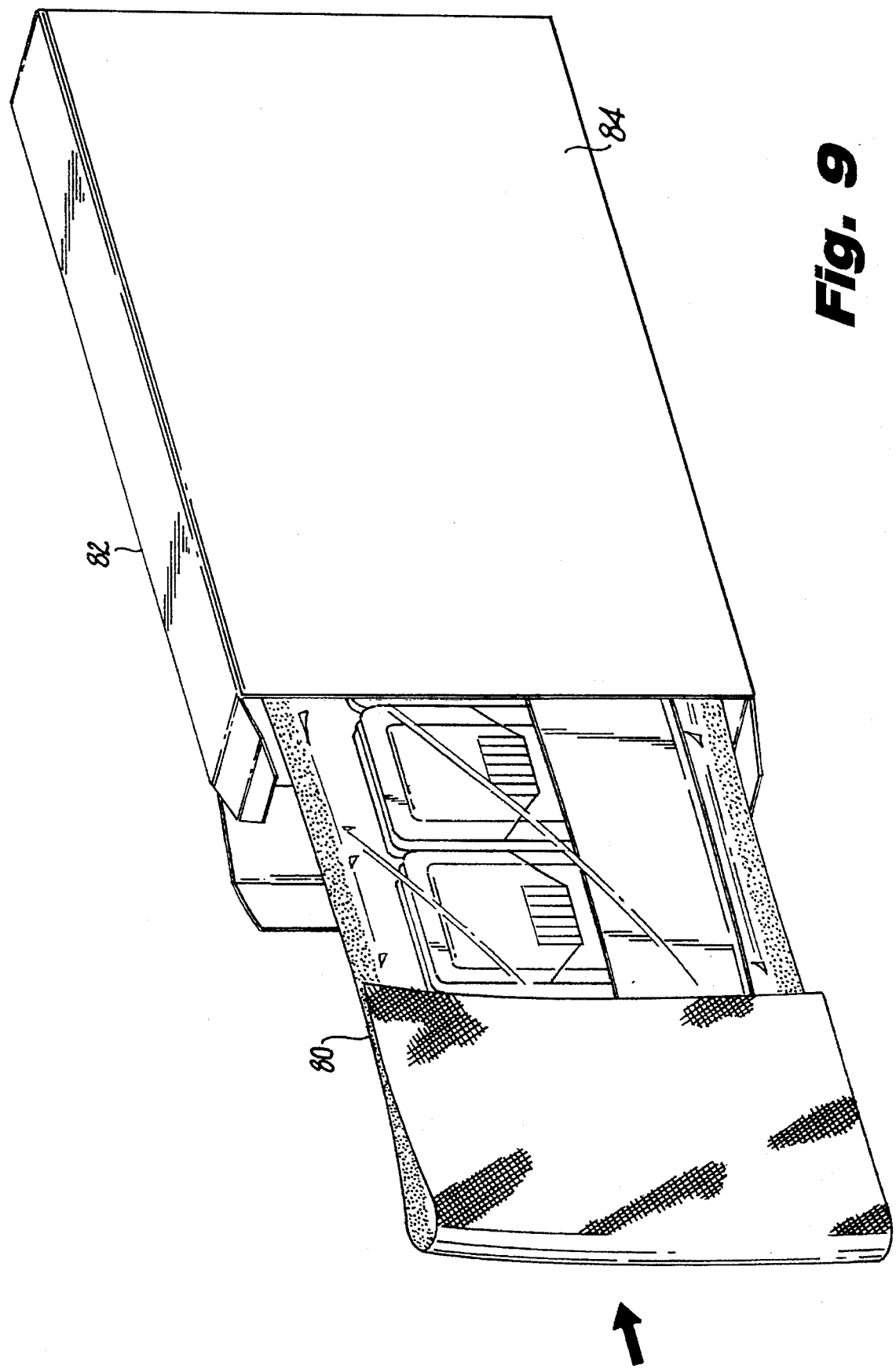

FIG. 6 is a perspective view similar to that of FIG. 4 illustrating and adjusting strap being inserted through a flap aperture;

FIG. 7 is a perspective view similar to FIG. 6 showing the adjusting strap being folded back and secured onto itself;

FIG. 8 is a perspective view of a suture package procedure kit including the embodiment of FIG. 4; and FIG. 9 is a perspective view of the suture package procedure kit of FIG. 8 being inserted into a storage and transportation box.

DETAILED DESCRIPTION OF PREFERRED EMBODIMENTS

Referring now to FIGS. 1 through 8 there is shown a suture package procedure kit suitable for retention, sterilization, storage and display of suture packages.

Referring initially to FIG. 1, there is shown a suture package sheath 20 which is designed to securely retain one or more suture packages during sterilization and subsequent transport and storage. In general, sheath 20 includes a front sheet 22 and a back sheet 24 joined together by any suitable means to define one or more suture package retention pockets or retaining portions 26 therein. Preferably sheets 22 and 24 are formed of a transparent or translucent plastic and are joined together by heat or R.F. sealing around outside edges thereof and along central portions to define retaining portions 26 therein. Sheaths 20 may be color coded to designate the type, style, or number of suture packages disposed therein. Alternatively, sheaths 20 may be formed of a paper material. Retaining portions 26 are dimensioned and configured to releasably and securely hold a suture package therein, such as for example, suture package 28. Preferably, raised area portions or locks 27 are formed in front sheet 22 or back sheet 24 and project into retaining portions 26. Locks 27 assist in securing suture package 28 within retaining portions by pinching or wedging against edges of suture packages 28. Additionally, a stiffening member 23 may be molded into a lower edge 25 of sheath 20 to provide structural support.

While sheath 20, including retaining portions 26, is dimensioned and configured to securely hold a suture package 28 therein, it is sometimes preferable to provide an additional retention member engagable with suture package 28 and sheath 20 to prevent suture package 28 from being shaken or jostled loose from retaining portions 26. The retention member preferably includes an adhesive retaining strip 30 which can be affixed to a back portion of suture package 28 and back panel 24 to secure suture package 28 within retaining portions 26. Preferably retaining strip 30 has a reduced area portion 31 which enables a user to break or tear strip 30 in order to facilitate removal of suture package 28 from retaining portions 26.

Often it is desirable to configure a suture package procedure kit with various numbers and types of suture packages. Thus the procedure kit may contain a plurality of sheaths 20, each containing differing numbers and types of suture packages 28. It is also desirable to join the various sheaths 20 together to facilitate sterilization, transportation and organization during use. To join sheaths 20 together a pair of joining apertures or holes 32 are formed in lower edge 25 of sheath 20 which, in conjunction with a linking member described in more detail herein below, are used to loosely hold a plurality of suture package sheaths 20 together.

While sheath 20 is illustrated as having two retaining portions 26 it will be appreciated that any suitable number of retaining portions 26 may be formed within a suture package sheath depending on the type, number and styles of suture packages to be inserted therein.

FIG. 2 illustrates another preferred embodiment of a suture package sheath. Sheath 34 is formed in essentially the same manner as sheath 20 and preferably contains four retaining portions 36 therein. Retaining portions 36 are dimensioned and configured to hold four suture packages 28. As with sheath 20, sheath 34 may utilize a retention member or retaining strip 30 to aid in securing suture packages 28 within retaining portions 36. Additionally, sheath 34 may contain a pair of joining apertures or holes 32 to link a series of sheaths 34 together.

Figure 3:
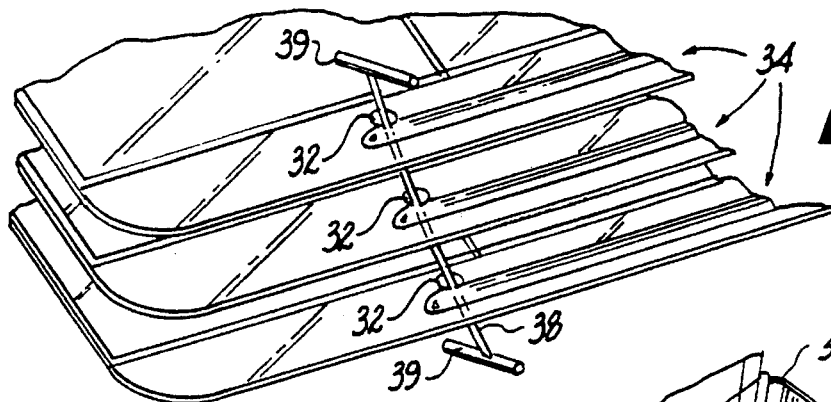
FIG. 3 is a partial perspective view of a plurality of suture package sheaths and an I-member securing them together.

As noted hereinabove, it is often preferable to join or link a series of suture package sheaths such as, for example, sheaths 34. Referring now to FIG. 3 there is disclosed an I-shaped linking member or tie 38 which is insertable through apertures 32 in sheaths 34 to link or stack together series of suture package sheaths 34. Preferably tie 38 has a pair of end portions 39 formed thereon which serve to anchor tie 38 against the outer sheaths in a group of stacked suture package sheaths 34.

Referring now to FIGS. 4 through 7 there is shown a preferred embodiment of an adjustable suture package sheath cover or retention sleeve 40, which may be used alone or in conjunction with tie 38, to retain one or more suture package sheaths. Sleeve 40 also provides the additional advantage of protecting a sterilization pouch, described in more detail below, from being punctured or torn by sheath 34 or tie 38.

Referring initially to FIG. 4, sleeve 40 generally includes first and second generally rectangular panels 42 and 44, respectively, which are foldably connected together along a fold line or fold area 46. When folded together in the direction of arrow A, first panel 42 and second panel 44 form a pocket 45 therebetween for receipt and support of one or more suture package sheaths such as, for example sheath 34 described hereinabove. To aid in holding second panel 44 adjacent first panel 42 there are provided a pair of interlocking end flaps formed at opposite end portions of first panel 42. First and second end flaps 48 and 50, respectively, are foldably connected to first panel 42 at fold areas 52, 54 respectively.

First and second flaps 48 and 50 are dimensioned and configured to interlock with one another so as to maintain second panel 44 adjacent first panel 42. Preferably first flap 48 has an aperture 56 formed therein and second flap 50 has an adjusting strap 60 extending therefrom. Adjusting strap 60 is insertable through aperture 56 to thereby interlock first and second flaps 48 and 50. In forming apeture 56 in first flap 48, a portion of first flap 48 is cut to result in a tab 57 (FIG. 6). When strap 60 is inserted through apeture 56, tab 57 folds back against first flap 48 to reinforce an edge of apeture 56 and help prevent tearing of first flap 48.

To facilitate interlocking first flap 48 with second flap 50, adjusting strap 60 is preferably provided with a first segment 62 and a second segment 64 foldably connected together along fold area 66. Upon insertion of strap 60 through aperture 56, second segment 64 may be folded back adjacent first segment 62 (FIG. 7) to thereby interlock flaps 48 and 50. By providing second segment 64 which may be folded back onto first segment 62 and tightened, the strap system may be assembled and tightened in one easy motion. Further, first and second segments, 62 and 64, respectively, provide a mechanical advantage in the form of a pully-like action which allows twice the holding force to be applied as opposed to a strap interlock system without such mechanical advantage. Various methods may be provided to secure second segment 64 to first segment 62, such as, for example, adhesive strips, tape or other grasping or locking methods.

Referring back to FIGS. 4 and 5, preferably first segment 62 is formed with one or more apertures 68. Second segment 64 is provided with a tab 70 which is engagable with apertures 68 to secure second segment 64 adjacent first segment 62. Second segment 64 may be formed with a fold area 72 adjacent to tab 70 in order flex or project tab 70 into aperture 68. As noted hereinabove sleeve 40 is adjustable so as to securely hold one or more suture package sheaths therein. Thus by providing a plurality of apertures 68, the size of the pocket 45 and the tension applied to first and second flaps 48 and 50, and thus to sheaths 20 and/or 34 contained therein, by strap 60 may be adjusted by inserting tab 70 into the appropriate aperture 68. Further, as tab 70 is inserted into various apertures 68, fold area 66 may vary along the length of strap 60.

Preferably, sleeve 40 is formed of a suitable gas permeable material. The preferred material is a spun bonded polyolefin fiber, such as, for example, Tyvek® 1073B available from E. I. DuPont de Nemours & Co. Other materials, both gas permeable and non-gas permeable may also be used.

Figure 5:
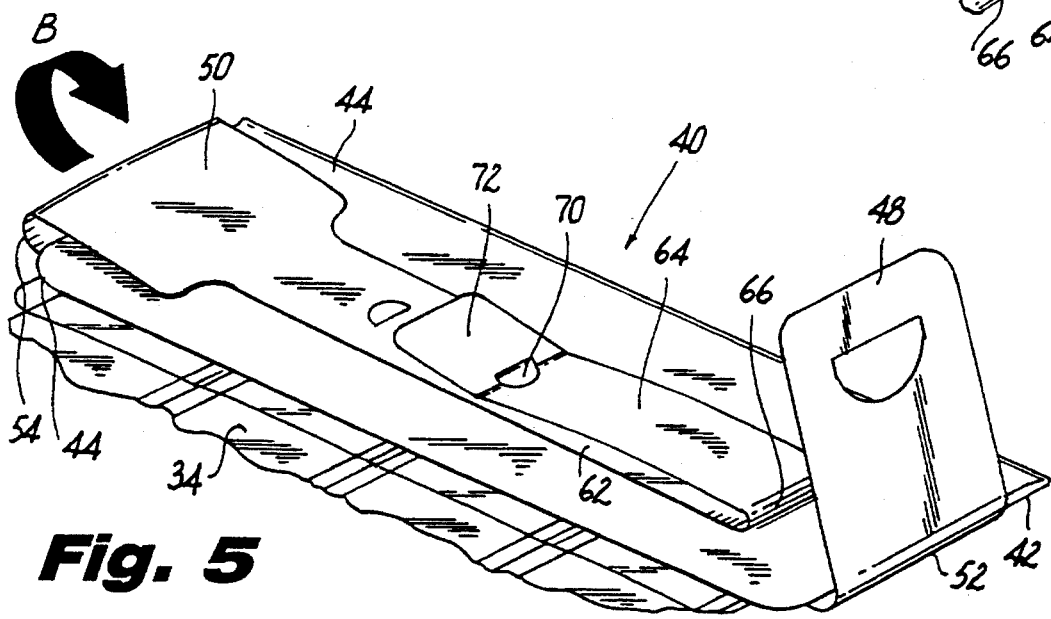
FIG. 5 is a perspective view of the embodiment of FIG. 4 with end flaps being folded over.

To assemble adjustable retention sleeve 40 about one or more suture package sheaths, such as, for example sheaths 20, sheaths 20 are initially positioned between first and second panels 42, 44, respectively, as shown in phantom in FIG. 4. Preferably sheaths 20 are initially held against first panel 42. Second panel 44 is folded towards first panel 42 along fold area 46 and around sheaths 20 in direction of arrow A to define pocket 45. As shown in FIG. 5, second flap 50 is folded over along fold area 54 such that adjusting strap 60 lies adjacent second panel 44. Second segment 64 of strap 60 is folded back along fold area 60 to lie adjacent first segment 62. Referring now to FIG. 6 adjusting strap 60 engages second panel 44 by insertion of second segment 64 through aperture 56. As second segment 64 is inserted through aperture 56 and pulled forward towards first segment 62, flap 48 is folded adjacent second panel 44. As noted hereinabove, this may be accomplished in one easy motion and will provide a high degree of holding power. As further shown in FIG. 6, second segment 64 is flexed along fold line 72 causing tab 70 to project therefrom. Referring now to FIG. 7, second segment 64 is pulled toward and folded adjacent first segment 62 and projecting tab 70 is inserted into an aperture 68 and folded flush along fold line 72 as indicated by arrow D. As noted hereinabove strap 60 and thus pocket 45 are adjustable by engagement of projecting tab 70 with the various apertures 68. In this manner the size of pocket 45 may be adjusted to securely retain one or more suture package sheaths disposed therein.

Referring now to FIG. 8, it is often desirable to provide a plurality of pre-selected and sterilized suture packages together in the form of a kit suitable for specific procedures. Thus, there may be provided a sterilization pouch such as for example, pouch 74. Pouch 74 generally includes a front cover 76 and a back cover 78 which are joined together by heat or R.F. sealing along outer edges thereof. Preferably front cover 76 is formed of a transparent, sterilizable plastic while back cover 78 is formed of a gas permeable material such as a Tyvek®.

In using the various components described herein various suture packages are selected depending on the type, number and styles sutures required. Suture packages 28 inserted into pockets 36 formed in sheaths 34. Preferably sheaths 34 are connected or linked together by joining member or tie 38. The adjustable suture package retention sleeve 40 is assembled about sheath 34 in the manner described hereinabove and adjusted to form the proper size pocket 45 between first panel 42 and second panel 44. Joined sheaths 34, loaded with suture packages 28, are thus secured within pocket 45 of sleeve 40. Descriptions of the type of suture packages may be indicated on an outer surface of first panel 42 or second panel 44. Sleeve 40, containing sheaths 34 and suture packages 28 are then inserted between front cover 76 and back cover 78 of pouch 74 which is then sealed closed. Preferably, top and side edges E and F of pouch 74, respectively, are sealed and sleeve 40 inserted into pouch 74. After insertion, a bottom edge G, of pouch 74 is sealed to thereby completely seal pouch 74. As noted hereinabove, sleeve 40 also acts as a shielding member to prevent ties 38 and/or sheaths 34 from puncturing pouch 74. Pouch 74, along with the contents thereof, are then sterilized using procedures known to those skilled in the art, such as, for example, by treating with ethylene oxide sterilizing gas or radiation. Once assembled, pouch 74 containing sleeve 40, sheaths 34 and suture packages 28, forms a suture package procedure kit 80 which may be sterilized, transported and stored. Referring to FIG. 9, in order to facilitate transportation of suture package procedure kit 80 and identification of the contents thereof, there is provide a box 82 for receipt of suture package procedure kit 80. Preferably the contents of suture package procedure kit 80 may be indicated on an outer surface 84 of box 82 utilizing known printing or labeling methods. Thus box 82 may be utilized to store and transport suture package procedure kit 80.

During an operation, sterilized suture package procedure kit 80 is removed from box 82 and pouch 74 opened to access the contents therein. Adjustable retention sleeve 40 can be removed and suture packages 28 displayed within sheaths 34. Alternatively, sheaths 34 can be displayed while retained within adjustable retention sleeve 40 or suture packages 28 can be completely removed from sheaths 34.

It will be understood that various modifications may be made to the embodiments disclosed herein. For example, various other methods of interlocking the end flaps of the adjustable retention sleeve may be provided, i.e., adhesive strips, etc. Additionally, the adjustable retention sleeve may be used alone to retain various suture packages and thus retention pockets may be formed within the sleeve. Therefore, the above description should not be construed as limiting, but merely as exemplifications of preferred embodiments. Those skilled in the art will envision other modifications within the scope and spirit of the claims appended hereto.

What is claimed is:

1. An adjustable sleeve for retaining suture package sheaths comprising:

a) a first panel having lower edge;

b) a second panel foldably interconnected to the first panel along the lower edge; and c) first and second flaps foldably formed on opposite end portions of the first panel, the first and second flaps configured for interlocking engagement such that when the second panel is folded adjacent the first panel and the first and second flaps are interlocked, the first and second interlocked flaps hold the second panel adjacent to the first panel to define the pocket, wherein the first flap has an aperture and the second flap has a strap extending therefrom, the strap configured for insertion through the aperture to thereby engage the first flap with the second flap.

2. The adjustable sleeve as recited in claim 1, wherein the strap includes a first segment and a second segment foldably connected to the first segment and releasably engagable therewith, such that when the strap is inserted through the aperture and the second segment is folded adjacent the first segment and engaged therewith, the first and second flaps are maintained in interlocking engagement.

3. The adjustable sleeve as recited in claim 2, wherein the first segment has an aperture formed therein and the second segment has a tab formed thereon and engagable with the aperture of the first segment to releasably engage the second segment with the first segment.

4. The adjustable sleeve as recited in claim 3, wherein the first segment has a plurality of apertures formed therein, the tab of the second segment being selectively engagable with any one of the plurality of apertures to vary the tension of the first and second segments apply to the first and second panels.

5. The adjustable sleeve as recited in claim 1, wherein the first and second panels are configured to support a plurality of suture package sheaths therebetween.

6. The adjustable sleeve as recited in claim 1, wherein the first and second panels and the first and second flaps are formed of a gas permeable material.

* * * * *